US006354837B1

(12) United States Patent
Jensen

(10) Patent No.: US 6,354,837 B1
(45) Date of Patent: Mar. 12, 2002

(54) METHOD FOR BLEACHING TEETH

(76) Inventor: Steven Jensen, 1190 W. Chauez Dr., South Jordan, UT (US) 84095

( * ) Notice: Subject to any disclaimer, the term of this patent is extended or adjusted under 35 U.S.C. 154(b) by 0 days.

(21) Appl. No.: 09/858,132

(22) Filed: May 15, 2001

(51) Int. Cl.[7] .................................................. A61C 5/00

(52) U.S. Cl. ......................... 433/215; 433/216; 433/80; 433/48

(58) Field of Search ............................ 433/37, 48, 215, 433/216, 229, 80

(56) References Cited

U.S. PATENT DOCUMENTS

| | | | | |
|---|---|---|---|---|
| 5,135,392 A | * | 8/1992 | Polansky | 433/37 |
| 5,165,424 A | * | 11/1992 | Silverman | 128/861 |
| 5,460,527 A | | 10/1995 | Kittelsen | 433/215 |
| 5,562,449 A | * | 10/1996 | Jacobs et al. | 433/215 |
| 5,846,082 A | * | 12/1998 | Thornton | 433/215 |
| 6,089,869 A | | 7/2000 | Schwartz | 433/215 |
| 6,116,900 A | | 9/2000 | Ostler | 433/89 |

OTHER PUBLICATIONS

Ultra–Form Vacuum Former and Ultra Vac advertisement (1 page).

* cited by examiner

*Primary Examiner*—Nicholas D. Lucchesi
(74) *Attorney, Agent, or Firm*—Daniel McCarthy

(57) ABSTRACT

A method for bleaching teeth is disclosed. The method includes the formation of a dental bleaching tray in a one step process that includes placing a moldable material adjacent teeth, permitting the moldable material to cure, and removing the cured moldable material which will then serve as a dental bleaching tray. Dental bleach may be placed into the dental bleaching tray and the tray may be placed onto teeth to accomplish bleaching. The entirety of the process may be performed at a patient's home or at a dental office, as desired.

5 Claims, 4 Drawing Sheets

METHOD FOR BLEACHING TEETH

BACKGROUND OF INVENTION

The invention relates to methods for bleaching teeth and the devices and substances used to perform such methods. More particularly, the invention relates to a more efficient, less expensive and less time consuming method for bleaching teeth that uses a formable substance to directly construct a dental bleaching tray rather than following the prior art steps of taking a dental impression, using the dental impression to form a mold, and using the mold to form a dental bleaching tray.

Dental bleaching is a well-known and economically important field. Increasingly, people are more concerned with maintaining an attractive personal appearance, and maintaining their teeth in good condition is critical to personal appearance. Of special importance is the color of a person's teeth. Various foods such as juices, coffee and tea cause discoloration or staining of human teeth. Other habits, such as smoking or chewing tobacco also cause tooth discoloration. Therefore it has become important in our society to address tooth discoloration issues by a process of dental bleaching.

In the prior art, dental bleaching was accomplished by obtaining a dental bleaching tray, placing a dental bleach such as carbamide peroxide or hydrogen peroxide into the tray, placing the dental bleaching tray over teeth so that the dental bleach contacts the teeth, and permitting the dental bleaching tray to remain in place for a desired period of time, such as 1 to 8 hours, while bleaching takes place. Sometimes the prior art used a light source or a heat source to accelerate bleaching.

The prior art dental bleaching trays were constructed according to a complex, time consuming and expensive multi-step process. A person desiring to whiten his or her teeth would make an appointment with a dental care provider. The dental care provider, after examining the patient's teeth, would take an impression of the patient's teeth using known dental impression materials, such as alginate. The dental impression materials were displaced by the patient's teeth and gums to form an accurate impression. It is well known that dental impressions can cause the patient discomfort and even pain.

After the dental impression was made, it was permitted to fully harden and was then transported to a dental laboratory. In the dental laboratory, a dental technician filled the dental impression with an appropriate mold making material such as stone gypsum. The mold making material would conform to the shape of the dental impression to accurately duplicate the shape of the patient's teeth and gums. Once hardened, the mold making material formed a mold of the patient's teeth and gums.

The mold was then placed onto a vacuum former adjacent a sheet of plastic. Under heat and vacuum, the plastic sheet closely adhered to the mold to form a dental bleaching tray that closely conformed to the patient's teeth and gums. The formed dental bleaching tray was then removed from the vacuum former and any excess plastic was trimmed from it. It was then transported to the dental care provider's office. At a mutually convenient date, the dental care provider would schedule another appointment with the patient and verify or adjust fit of the dental bleaching tray. Thereafter, the dental bleaching tray could be used for dental bleaching performed by the patient at home or performed by the dental care provider in his or her office.

From the above description, it can be seen that the process of forming a dental bleaching tray was very time consuming, labor intensive and expensive, requiring at least two visits to the dental care provider's office by the patient and work by a dental laboratory technician. Typically at least two weeks would pass between the patient's request for a dental bleaching tray and its delivery to the patient.

There is a demand for dental bleaching trays which can be fabricated immediately by a dental care provider or a patient without the use of a dental laboratory or a dental laboratory technician, and that do not include the great amounts of time and labor that the prior art processes require.

SUMMARY OF INVENTION

It is an object of the invention to provide a method by which a dental bleaching tray may be formed directly by impressing a person's teeth into a moldable material without intermediate mold forming and molding steps as seen in the prior art.

Additional objects, features and advantages of the invention will become apparent to the reader on reading the patent specification in light of the appended drawings.

DETAILED DESCRIPTION

The first step in forming a dental bleaching tray according to the invention is to select a material that may be molded into the desired dental bleaching tray. It is desired to avoid use of a mold, heat or vacuum to form the dental bleaching tray in order to overcome problems of the prior art. Therefore, the inventor has found it is most desirable to utilize a material which is soft and flowable under pressure yet will harden quickly to form the dental bleaching tray.

Examples of such materials include polyvinyl siloxane, polyether cement, alginate, and other suitable materials. Typically such materials are two part mixtures consisting of a base and a catalyst which must be kept separated until immediately before use or they will react and cure prior to use. Although the invention does not require a 2 part composition, most of the practical and available moldable materials perform best if used in a 2 part configuration.

The two parts of the moldable material may be mixed in any desired manner, such as in a mixing dish, by use of a double barrel syringe equipped with a mixing tip, or according to other methodologies. For convenience, the inventor contemplates that most users of the invention will prefer use of a double barrel syringe for storing the 2 constituents of the moldable material in unmixed form and for dispensing the moldable material in a mixed form ready to use.

Figure 1:
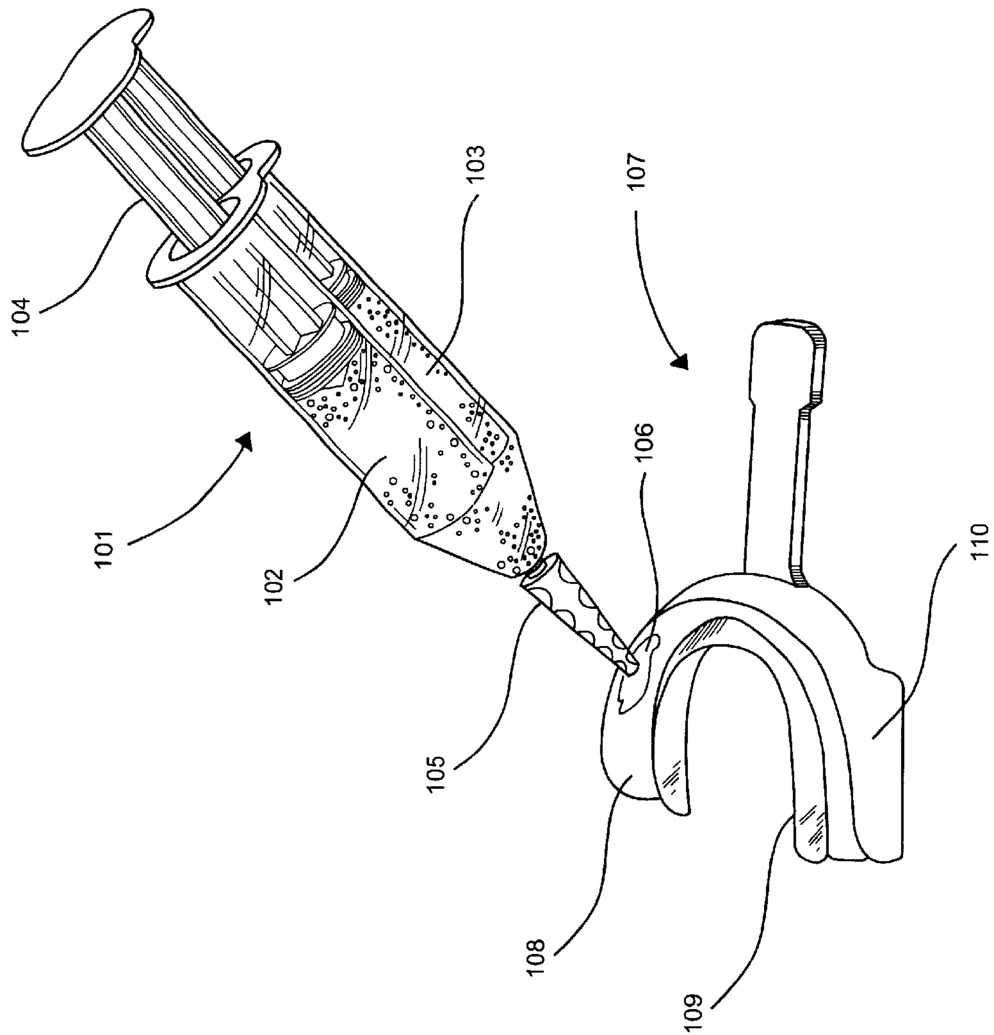
FIG. 1 depicts a moldable material of the invention being placed into a dental tray.

Referring to FIG. 1, a depiction is provided of a moldable material of the invention being placed into a dental tray prior to formation of the dental bleaching tray. A double barrel syringe 101 having a first chamber 102 containing a base and a second chamber 103 containing a catalyst of the moldable material. A plunger 104 of the double barrel syringe is used to force the base and the catalyst through a mixing tip 105 so that a mixed moldable material 106 is placed into a dental tray 107. The dental tray 107 can be any prior art or suitable dental impression tray, such as a metal tray or disposable plastic tray. The dental tray 107 has a trough 108 for receiving the moldable material 106 and side walls 109 and 110 for containing the moldable material. Once an adequate amount of moldable material 106 has been dispensed from the double barrel syringe, the double barrel syringe may be stored for later use and the next step of forming a dental bleaching tray may be performed.

Figure 2:
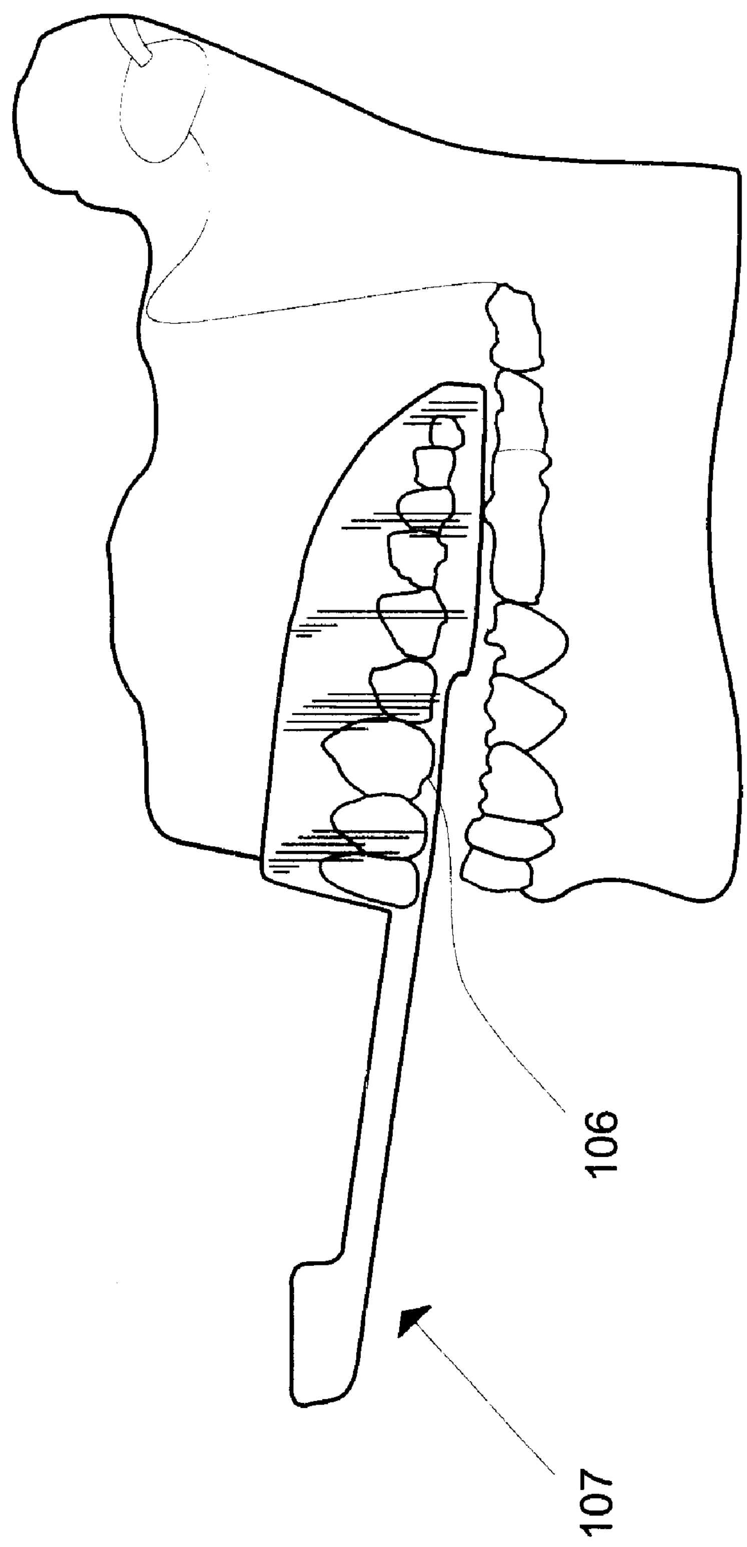
FIG. 2 depicts use of a moldable material to directly form a dental bleaching tray by pressing a person's teeth into the moldable material.

FIG. 2 depicts use of a moldable material to directly form a dental bleaching tray by pressing a person's teeth into the moldable material. The dental tray 107 is depicted with moldable material 106 being forced to assume the contour of the patient's teeth and gums. When the tray 107 is placed into the patient's mouth, the patient will bite into it to force the moldable material around the teeth and gums. The dental tray 107 may be made of a clear material for viewing purposes and the moldable material may be clear, opaque or translucent as desired to aid in observing the molding process. The dental tray 107 is kept in place in the patient's mouth until the moldable material is cured, typically two to six minutes time.

Figure 3:
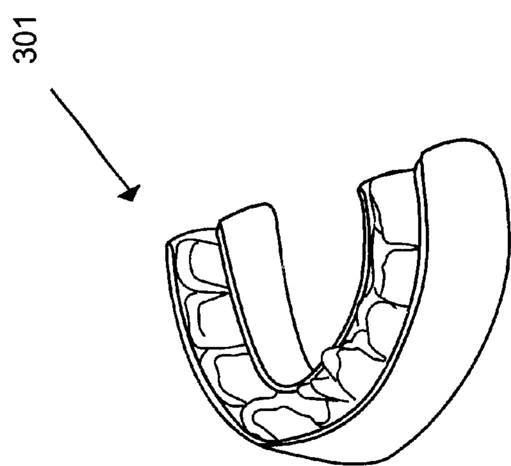
FIG. 3 depicts a finished dental bleaching tray of the invention.

When the curing process is complete, the tray 107 is removed from the patient's mouth and the formed dental bleaching tray 301 as depicted in FIG. 3 is removed. Any excess material on the dental bleaching tray may be trimmed from it. The dental bleaching tray will have outer walls of a thickness determined by the difference between the dimension of the dental tray 107 and the size of the patient's teeth and gum structures. However, the fit of the interior of the dental bleaching tray 301 and the teeth will be exact so that dental bleaching may be performed with a minimal amount of bleach. The dental bleaching tray 301 formed from preferred moldable materials will be somewhat soft and flexible.

Figure 4:
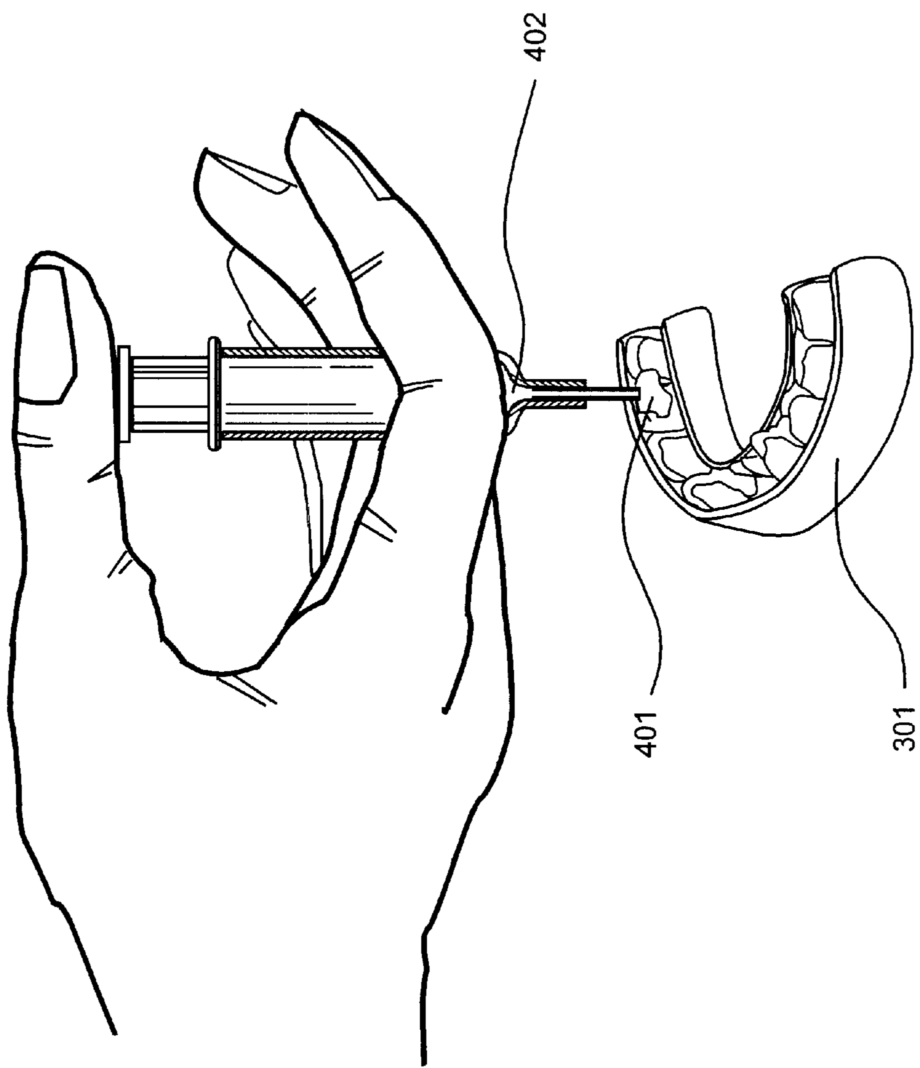
FIG. 4 depicts placing a dental bleach into the dental bleaching tray.

Once the dental bleaching tray 301 is formed, a quantity of dental bleach 401 may be placed within it as depicted in FIG. 4. The dental bleach may be a single component bleach or a dual component bleach. The bleach may be a pre-mixed bleach or a bleach prepared on site just prior to use. Commonly dental bleaches are dispensed into dental bleaching trays using a single or double barrel syringe. For purposes of illustration, dispensation of dental bleach 401 into dental bleaching tray 301 using a single barrel syringe 402 is depicted.

Figure 5:
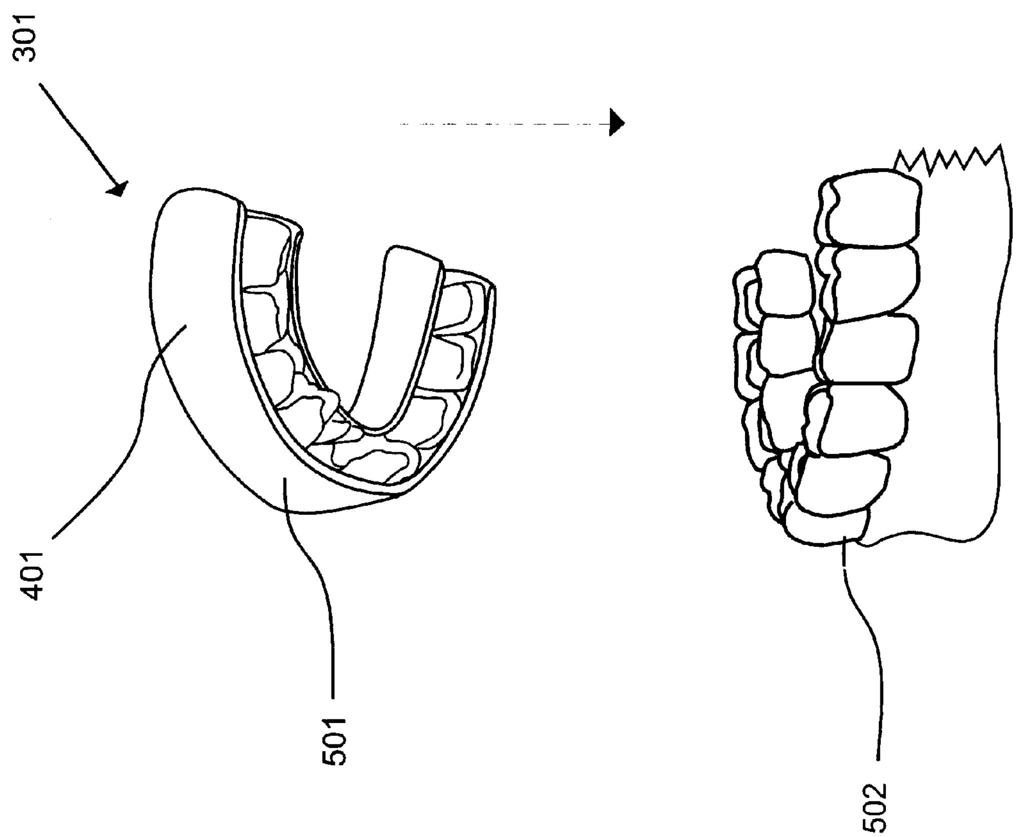
FIG. 5 depicts a dental bleaching tray of the invention being placed onto teeth for use.

Referring to FIG. 5, the dental bleaching tray 301 containing a quantity of desired dental bleach dispensed therein 401 across the entire arch 501 is placed onto the dentrifice 502 of a patient and permitted to remain there for a desired period of time for bleaching to occur. As desired, the dental bleach may be exposed to light or heat at this stage in order to accelerate bleaching.

Finally, the dental bleaching tray 301 is removed from the teeth and it and the teeth may be rinsed. Repeated bleaching applications will improve results obtained.

While the present invention has been described and illustrated in conjunction with a number of specific embodiments, those skilled in the art will appreciate that variations and modifications may be made without departing from the principles of the inventions as herein illustrated, described and claimed.

The present invention may be embodied in other specific forms without departing from their spirit or characteristics. The described embodiments are to be considered in all respects as only illustrative, and not restrictive. The scope of the invention is, therefore, indicated by the appended claims, rather than the foregoing description. All changes that come within the meaning and range of equivalency of the claims are to be embraced within their scope.

What is claimed is:

1. A method for bleaching teeth comprising the steps of:

obtaining a dental tray having a trough in which a moldable material may be deposited, selecting a moldable material having a two part composition, said first part being a base and said second part being a catalyst, mixing said first part and said second part of said moldable material, placing a quantity of said moldable material in said trough of said dental tray, placing said dental tray into a patient's mouth and pressing the patient's teeth into said moldable material, maintaining the patient's teeth in said moldable material until said moldable material is substantially cured to form a dental bleaching tray, removing said dental tray having said dental bleaching tray formed in it, removing said dental bleaching tray from said dental tray, placing a quantity of dental bleach into said dental bleaching tray, placing said dental bleaching tray onto teeth to be bleached so that said dental bleaching tray maintains said dental bleach in contact with teeth, permitting said dental bleach to exert a whitening effect on the teeth, removing said dental bleaching tray from the teeth.

2. A method as recited in claim 1 wherein said moldable material is selected from the group consisting of polyvinyl siloxane and polyether cement.

3. A method as recited in claim 1 further comprising the step of trimming excess material from said dental bleaching tray.

4. A method as recited in claim 1 wherein said mixing step is performed by use of a double barrel syringe, said double barrel syringe having a first chamber for storing said base and a second chamber for storing said catalyst and a mixing tip for mixing said base and said catalyst when said base and said catalyst are dispensed from said syringe so that a fully mixed moldable material is dispensed from said syringe.

5. A method for forming a dental bleaching tray useful for bleaching teeth, the method comprising the steps of:

obtaining a dental tray having a trough in which a moldable material may be deposited, selecting a moldable material having a two part composition, said first part being a base and said second part being a catalyst, mixing said first part and said second part of said moldable material, placing a quantity of said moldable material in said trough of said dental tray, placing said dental tray into a patient's mouth and pressing the patient's teeth into said moldable material, maintaining the patient's teeth in said moldable material until said moldable material is substantially cured to form a dental bleaching tray.

* * * * *